United States Patent
Babu et al.

(10) Patent No.: US 9,212,386 B2
(45) Date of Patent: Dec. 15, 2015

(54) ENZYMATIC CLEAVAGE BASED LATERAL FLOW ASSAYS

(75) Inventors: Uma Mahesh Babu, Bradenton, FL (US); Robert P. Sambursky, Bradenton, FL (US); Robert W. VanDine, Montoursville, PA (US)

(73) Assignee: Rapid Pathogen Screening, Inc., Sarasota, FL (US)

( * ) Notice: Subject to any disclaimer, the term of this patent is extended or adjusted under 35 U.S.C. 154(b) by 156 days.

(21) Appl. No.: 13/553,011

(22) Filed: Jul. 19, 2012

(65) Prior Publication Data

US 2014/0227773 A1 Aug. 14, 2014

Related U.S. Application Data

(60) Provisional application No. 61/510,681, filed on Jul. 22, 2011.

(51) Int. Cl.
| | |
|---|---|
| *C12Q 1/37* | (2006.01) |
| *B01L 3/00* | (2006.01) |
| *G01N 33/00* | (2006.01) |
| *G01N 33/52* | (2006.01) |

(52) U.S. Cl.
CPC ............... *C12Q 1/37* (2013.01); *G01N 33/521* (2013.01); *G01N 33/523* (2013.01)

(58) Field of Classification Search
CPC ..... C12Q 1/37; G01N 33/523; G01N 33/521; B01L 3/5027; B01L 3/502769
See application file for complete search history.

(56) References Cited

U.S. PATENT DOCUMENTS

| | | | |
|---|---|---|---|
| 2002/0192789 A1* | 12/2002 | Ley et al. ................ | 435/194 |
| 2008/0145843 A1 | 6/2008 | Song | |
| 2009/0203059 A1 | 8/2009 | Davis et al. | |
| 2009/0253119 A1 | 10/2009 | Zhou et al. | |
| 2011/0086359 A1 | 4/2011 | Babu et al. | |
| 2011/0086370 A1 | 4/2011 | Schouten | |
| 2011/0136258 A1 | 6/2011 | Sambursky et al. | |
| 2013/0122043 A1* | 5/2013 | Guimaraes et al. ....... | 424/204.1 |

FOREIGN PATENT DOCUMENTS

| | | |
|---|---|---|
| EP | 2189536 A1 | 5/2010 |
| WO | 9416108 A1 | 7/1994 |

OTHER PUBLICATIONS

Anne E. Boyer et. al., "Detection and Quantification of Anthrax Lethal Factor in Serum by Mass Spectrometry." Anal. Chem., 2007, 79, pp. 8463-8470.

(Continued)

*Primary Examiner* — Nathan Bowers
(74) *Attorney, Agent, or Firm* — Brown & Michaels, PC

(57) ABSTRACT

Methods and devices for detecting a target enzyme include an anchored or trapped peptide complex. The peptide complex includes an anchor particle immobilized on a sample analysis device or trapped in a reaction receptacle including a filter, a peptide, with at least one enzyme cleavage site for a target enzyme, bound to the anchor particle, at least one detectable label, and at least one first tag bound to the peptide on a side of the enzyme cleavage site opposite the anchor particle. When the target enzyme is present in the sample, the enzyme cleaves the peptide at the enzyme cleavage site, permitting the cleaved peptide to reach the test zone of a sample analysis device such that the first tag binds to the immobilized second tag and a signal is detected at the test zone.

15 Claims, 9 Drawing Sheets
(7 of 9 Drawing Sheet(s) Filed in Color)

(56) References Cited

OTHER PUBLICATIONS

International Search Report and Written Opinion for PCT/US2012/047321, issued on Jan. 25, 2013.

Extended European Search Report for PCT/US2012047321; Feb. 12, 2015; 6 pages.

* cited by examiner

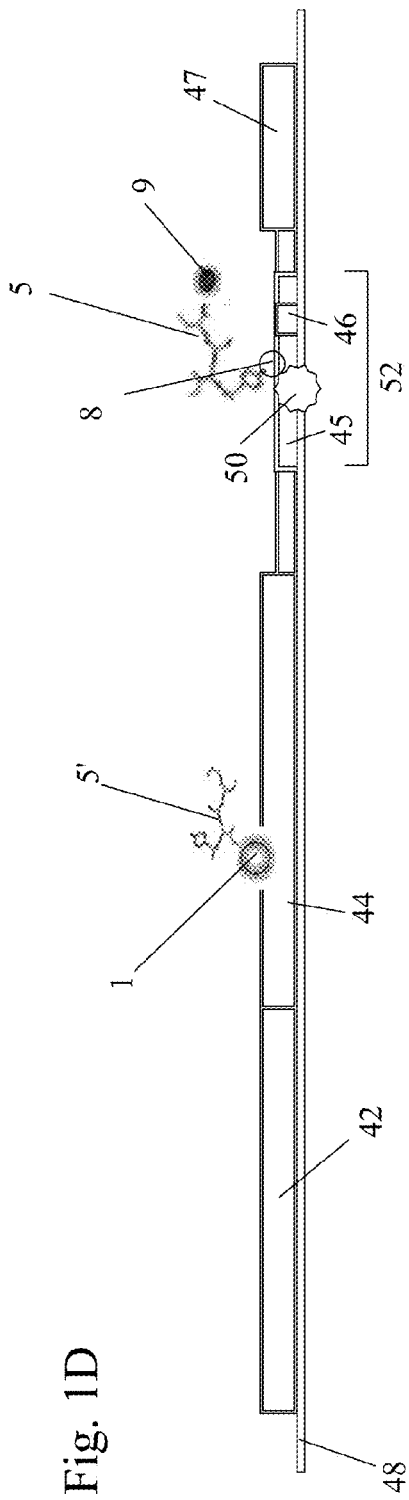

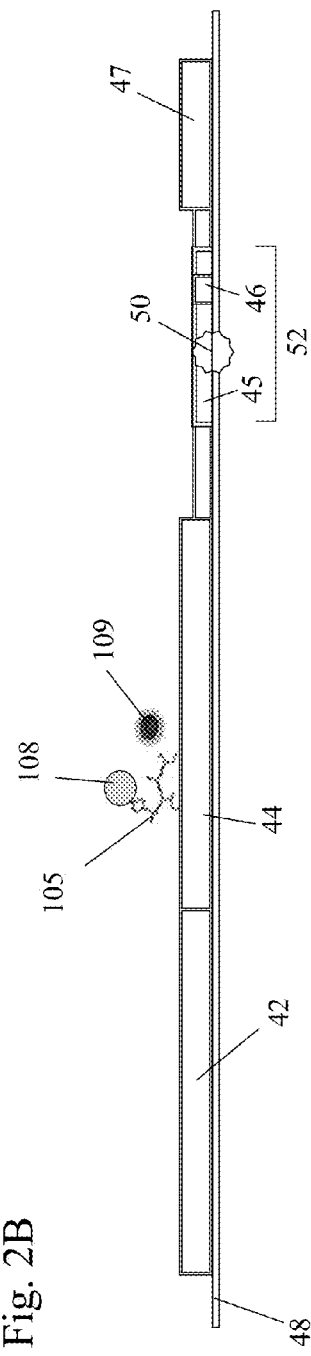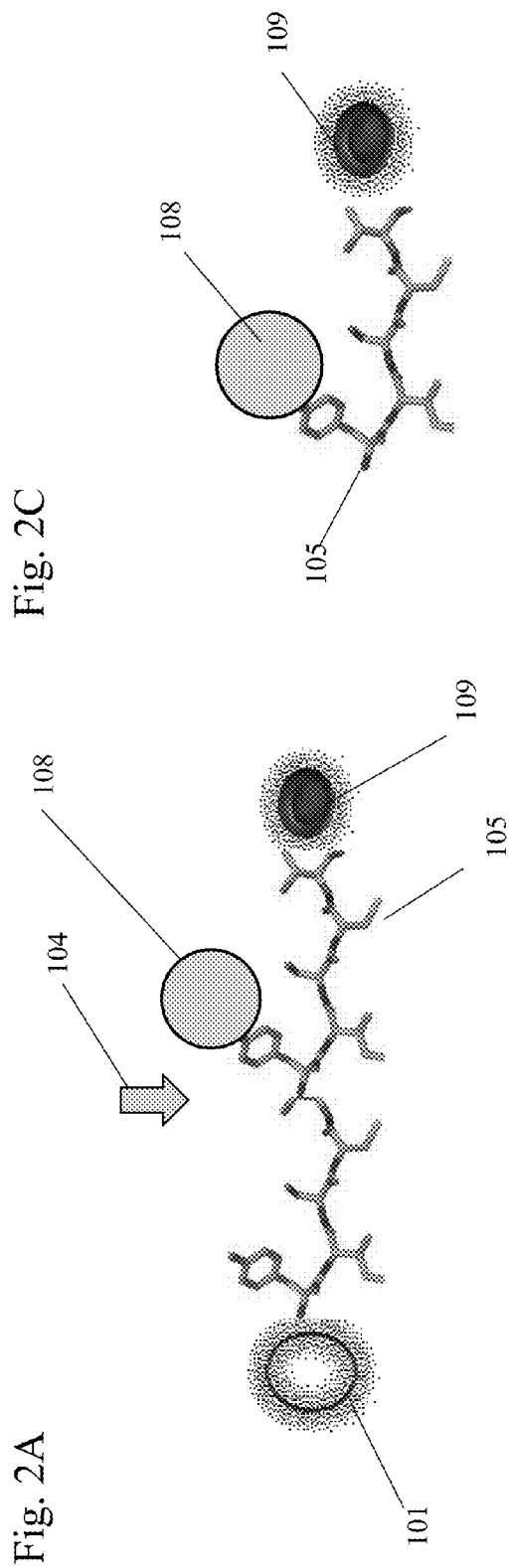
Fig. 2B
Fig. 2C
Fig. 2A

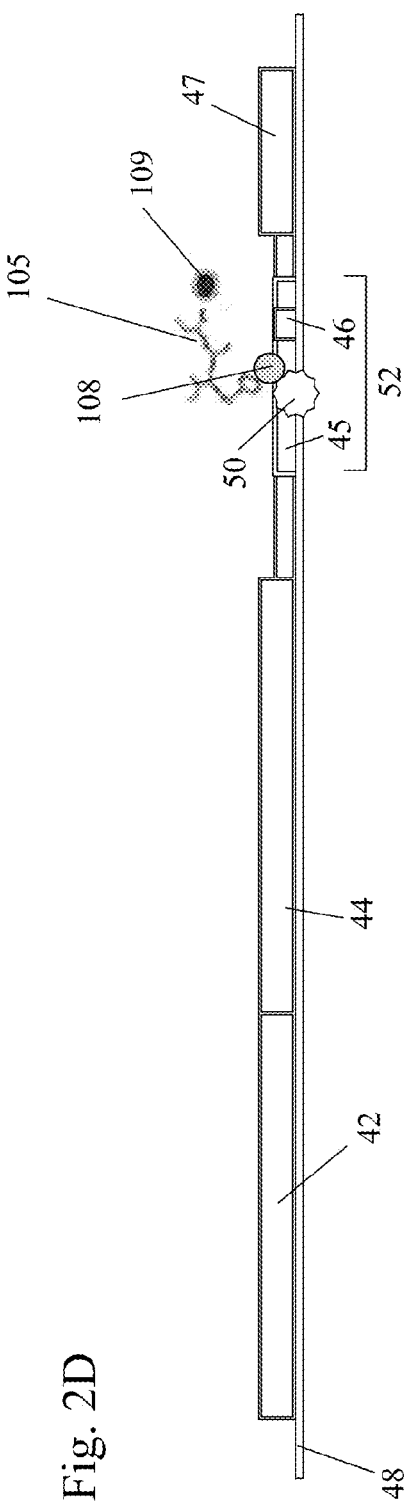

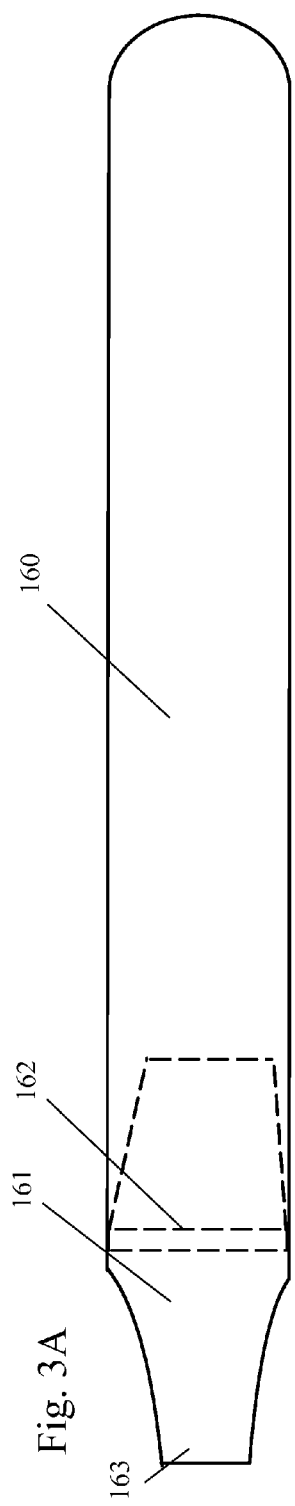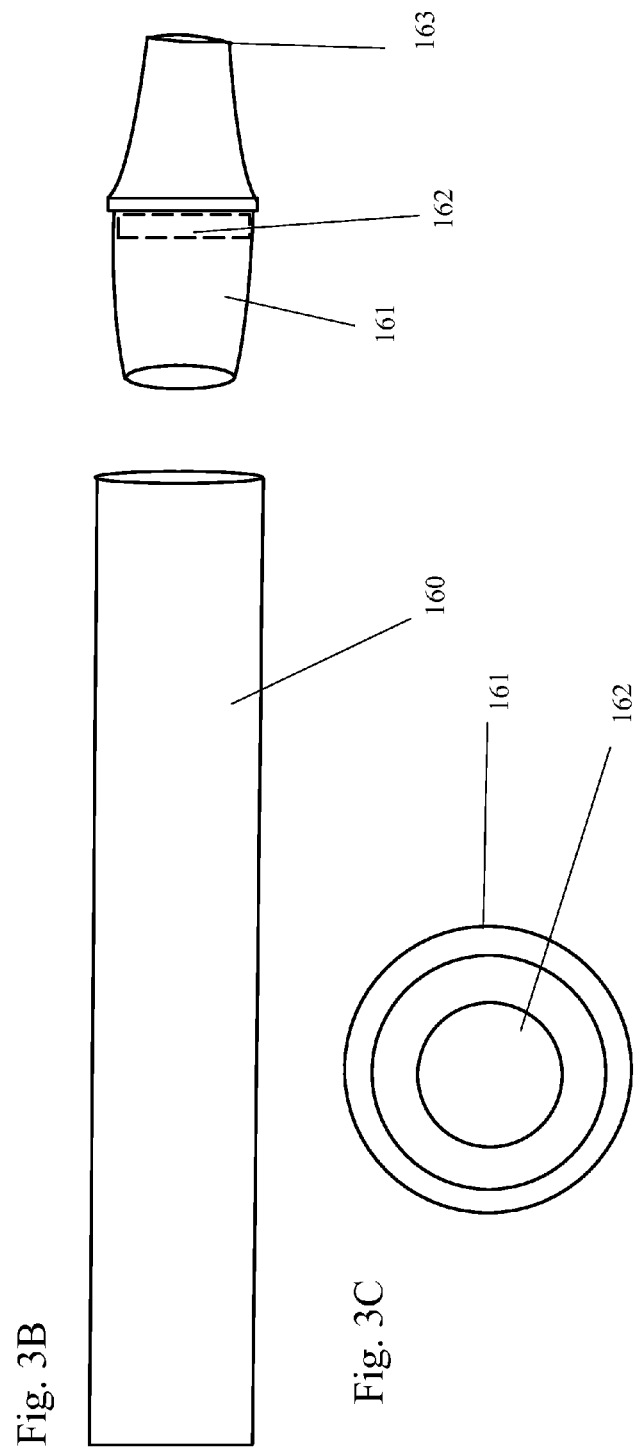
Fig. 3A
Fig. 3B
Fig. 3C

US 9,212,386 B2

ENZYMATIC CLEAVAGE BASED LATERAL FLOW ASSAYS

REFERENCE TO RELATED APPLICATIONS

This application claims one or more inventions which were disclosed in Provisional Application No. 61/510,681, filed Jul. 22, 2011, entitled "ENZYMATIC CLEAVAGE BASED LATERAL FLOW ASSAYS". The benefit under 35 USC §119(e) of the United States provisional application is hereby claimed, and the aforementioned application is hereby incorporated herein by reference.

BACKGROUND OF THE INVENTION

1. Field of the Invention

The invention pertains to the field of point of care tests. More particularly, the invention pertains to lateral flow assays.

2. Description of Related Art

Lateral flow assays are a subset of assays combining various reagents and process steps in one assay strip, thus providing a sensitive and rapid mechanism for the detection of target molecules. Antibody-based lateral flow immunoassays are available for a wide range of target analytes and can be designed for sandwich or competitive test principles. Generally, high molecular weight analytes with several epitopes are analyzed in a sandwich format whereas small molecules representing only one epitope are detected by means of a competitive assay. The first tests were made for human chorionic gonadotropin (hCG). Today there are commercially available tests for monitoring ovulation, detecting infectious disease organisms, analyzing drugs of abuse, and measuring other analytes important to human physiology. Products have also been introduced for veterinary testing, environmental testing, and product monitoring.

SUMMARY OF THE INVENTION

In some preferred embodiments, methods and devices for detecting a target enzyme include an anchored peptide complex. The anchored peptide complex includes an anchor particle immobilized on a lateral flow assay device, a peptide reversibly bound to the anchor particle with at least one enzyme cleavage site for a target enzyme, at least one detectable label, and at least one first tag bound to the peptide on a side of the enzyme cleavage site opposite the anchor particle. The detectable label is preferably either a dye that dyes the peptide or a label bound to the peptide on a side of the enzyme cleavage site opposite the anchor particle or coupled to the peptide. The assay device also includes a test zone comprising at least one second immobilized tag that binds to the first tag. When the target enzyme is present in the sample, the enzyme cleaves the peptide at the enzyme cleavage site, the tagged and labeled peptide is released from the anchor, and the first tag moves and binds to the immobilized second tag in the test zone.

In other preferred embodiments, a lateral flow assay system for detecting a target enzyme in a sample includes a reaction receptacle and a sample analysis device. The reaction receptacle preferably includes a chamber for reaction between the sample and a trapped peptide complex, which includes a trappable particle, a peptide reversibly bound to the trappable particle, where the peptide includes at least one enzyme cleavage site for a target enzyme, at least one detectable label, and at least one first tag bound to the peptide on a side of the enzyme cleavage site opposite the trappable particle. The detectable label is preferably either a dye that dyes the peptide or a label bound to the peptide on a side of the enzyme cleavage site opposite the trappable particle or coupled to the peptide.

The reaction receptacle also includes at least one filter with a pore size that is smaller than the size of the trappable particle. The sample analysis device includes a sample application zone for receiving the reacted sample and peptide from the reaction receptacle and a test zone including at least one immobilized second tag that binds to the first tag. When the target enzyme is present in the sample, the enzyme cleaves the peptide at the enzyme cleavage site such that the peptide can pass through the filter and be transferred from the reaction receptacle to the sample application zone of the sample analysis device, and the first tag binds to the immobilized second tag in the test zone such that the label is detectable in the test zone. When the target enzyme is not present in the sample, the peptide is trapped in the reaction receptacle by the filter and is not transferred to the sample analysis device, and there is no detectable signal in the test zone when an assay has been run.

BRIEF DESCRIPTION OF THE DRAWINGS

The patent or application file contains at least one drawing executed in color. Copies of this patent or patent application publication with color drawings will be provided by the Office upon request and payment of the necessary fee.

FIG. 1D shows a test strip with the peptide of FIG. 1C bound to the test zone through an interaction between two tags after the peptide has been cleaved from the anchor particle by the target enzyme.

FIG. 2A shows a peptide bound to a trappable particle in an embodiment of the present invention.

FIG. 2B shows a test strip after a cleaved labeled peptide has been placed on the strip in an embodiment of the present invention.

FIG. 2C shows the peptide of FIG. 2A after cleavage by a target enzyme in an embodiment of the present invention.

FIG. 2D shows a test strip with the peptide of FIG. 2C bound to the test zone through an interaction between two tags in an embodiment of the present invention.

FIG. 3A shows an assembled tube and dropper in an embodiment of the present invention.

FIG. 3B shows a separate tube and dropper in an embodiment of the present invention.

FIG. 3C shows an interior of the dropper of FIGS. 3A and 3B in an embodiment of the present invention.

Figure 1B:
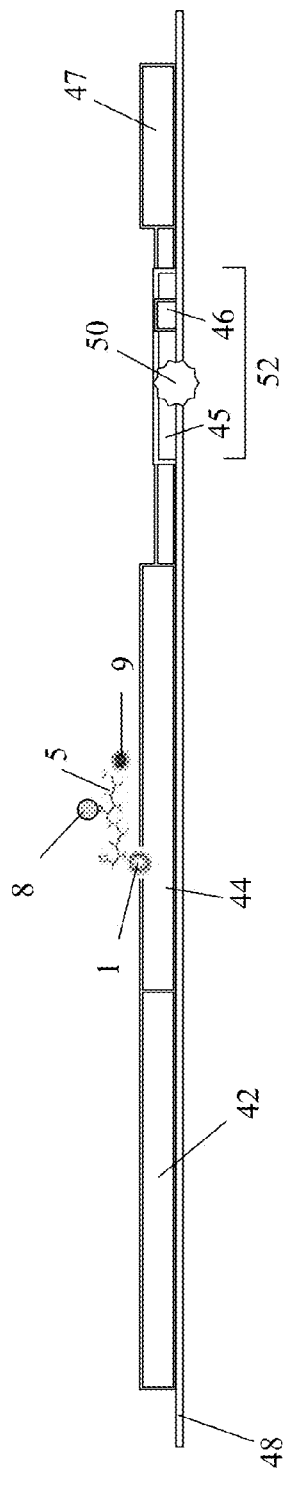
FIG. 1B shows a test strip with the anchor particle and peptide trapped in the sample zone of the test strip in an embodiment of the present invention.

Note that the figures are not drawn to scale.

DETAILED DESCRIPTION OF THE INVENTION

In one embodiment of the present invention, peptides engineered to have one or more enzyme cleavage sites are used to identify the presence of one or more enzymes in a sample, termed Specific Peptide Enzyme Chromatography (SPEC) herein. These assays preferably require no antibodies.

FIGS. 1A through 1D show an example of an embodiment of the system with an anchored peptide with an enzyme cleavage site and a sample analysis device (a test strip in the figure). The test strip preferably includes an absorbent pad 42, a sample application zone 44, a detection zone 52, and an optional waste pad 47. The test strip also preferably includes a carrier backing 48.

Figure 1C:
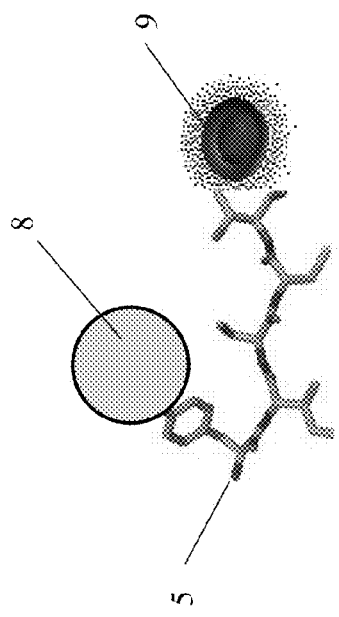
FIG. 1C shows the peptide of FIG. 1A after cleavage by a target enzyme in an embodiment of the present invention.
Figure 1A:
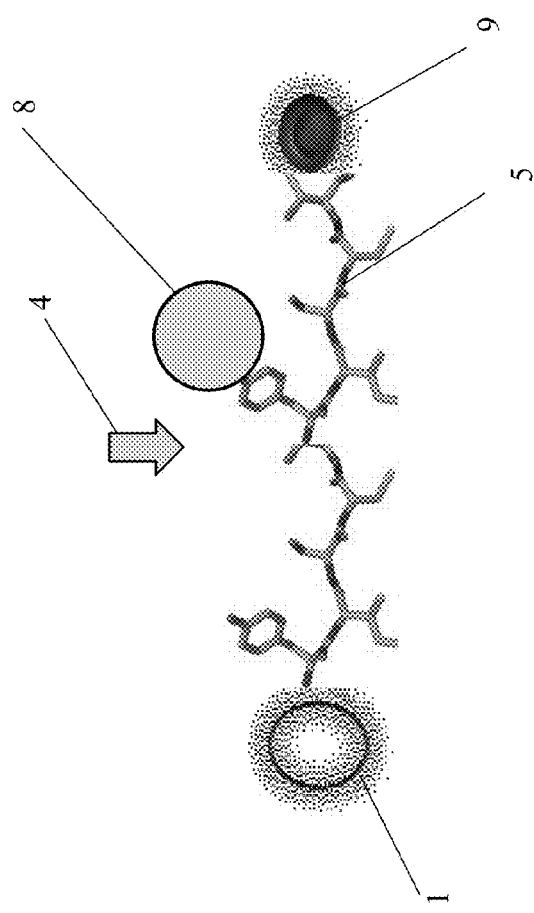
FIG. 1A shows a peptide bound to an anchor particle in an embodiment of the present invention.
Figure 4:
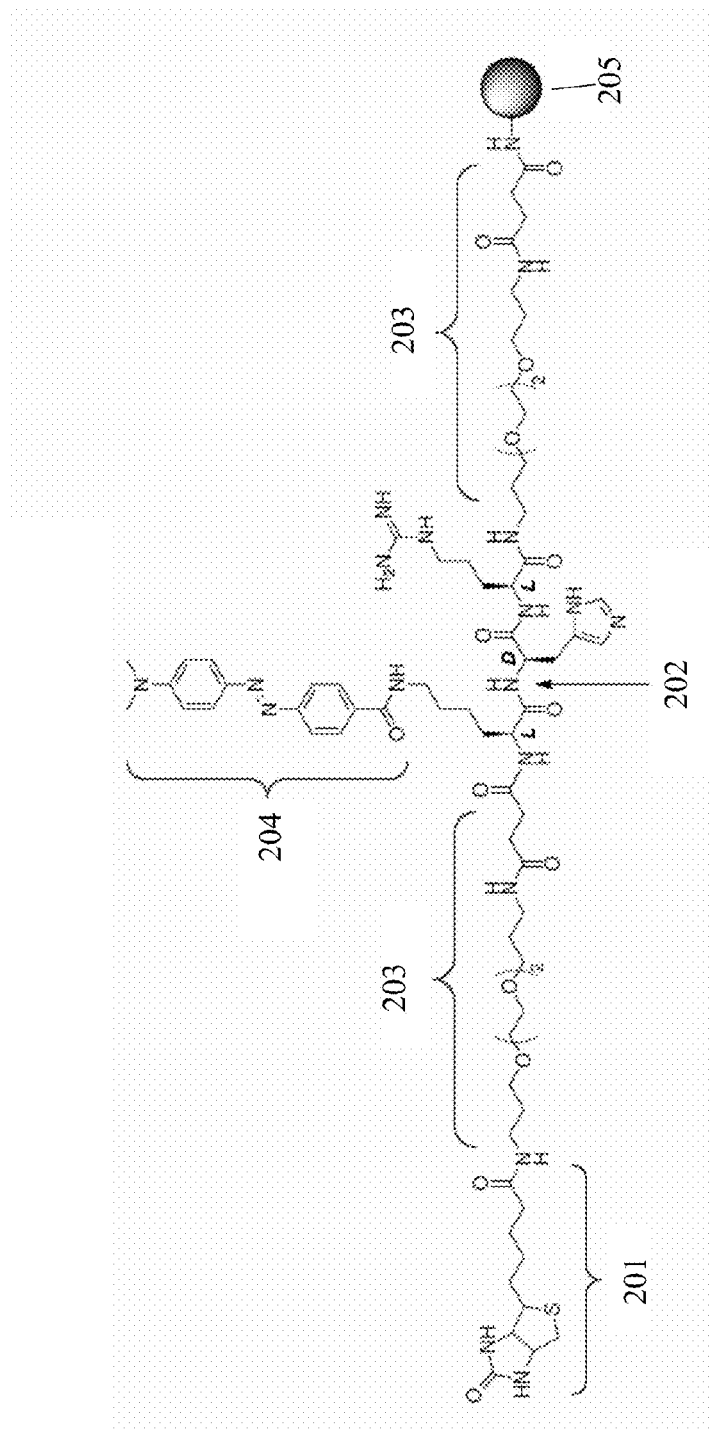
FIG. 4 shows the structure of the substrate NMFB1.

The anchored peptide complex, shown in FIG. 1A, includes an anchor particle 1, preferably at least 10 μm in size, that is trapped on the test strip. In the embodiment shown in FIG. 1B, the anchor particle 1 is bound in the sample application zone 44. The size of this particle 1 depends upon the porosity of the membrane. Any particle that is greater or equal to the porosity of the membrane can act as the anchor particle 1.

Although the anchor particle 1 is shown in the sample application zone 44 in this figure, the anchor particle 1 may alternatively be located anywhere on the test strip where it will encounter the sample as the sample is eluted through the test strip. These locations include where the sample is added, or somewhere downstream of where the sample is added but upstream of or in the detection zone.

The anchor particle 1 is bound to a peptide 5, which is preferably approximately 20 to 30 amino acids long. The peptide 5 includes at least one enzyme cleavage site 4. The enzyme cleavage site is specific to a target enzyme. For example, the enzyme may be specific to a bacteria that causes infection. One can choose a peptide 5 that is cleavable by an enzyme ubiquitous in many different bacterial strains, or an enzyme that is only found in one or two strains of bacteria. Peptides may be selectively engineered for one or two strains. The peptide may be made as specific as needed for the assay. The specificity of the assay depends on the enzyme chosen. For example, some enzymes are specific for multiple strains of bacteria, while other enzymes are specific to one or two particular strains of the bacteria. In other embodiments, the enzymes being tested for may be from viruses, or other sample components of interest.

The peptide 5 is also bound to a tag 8 and a detectable label 9. In preferred embodiments, the detectable label 9 is a visible label, but other labels, as known in the art, could be used. In one preferred embodiment, a gold label is used. In another embodiment, instead of being bound to a detectable label 9, the peptide 5 is dyed with a detectable label. The tag 8 and the label 9 are both bound to the peptide 5 at a location on the side of the enzyme cleavage site opposite the side where the anchor particle 1 is located.

When the target enzyme is present in the sample, the enzyme cleaves the peptide 5 at the enzyme cleavage site 4. The cleavage results in the portion of the peptide 5 no longer attached to the anchor particle 1 being mobile, and it travels downstream to the detection zone 52. This peptide portion is shown in FIGS. 1C and 1D. There is an immobilized tag 50 in the test zone 45, which binds to the tag 8 on the peptide. The remainder of the peptide 5' remains bound to the anchor particle 1 in the sample application zone 44.

In one preferred embodiment, the peptide 5 is tagged with biotin 8. In embodiments where the tag 8 on the peptide 5 is biotin, the immobilized tag 50 in the detection zone is preferably avidin, neutravidin, or streptavidin. In other embodiments, the peptide 5 is tagged 8 with avidin, neutravidin, or streptavidin. In these embodiments, the immobilized tag 50 in the detection zone 52 is preferably biotin. Alternatively, the tag 8 on the peptide may be a lectin and the immobilized tag 50 may be a glycosyl moiety. For example, in some embodiments, the lectin is the Garden pea Lectin and the glycosyl moiety is an erythrocyte glycosyl unit. The tag on the peptide and the immobilized tag may be reversed within the spirit of the present invention. For example, the glycosyl moiety may be the tag on the peptide, with an immobilized lectin tag in the detection zone. In other embodiments, other receptors and ligands may be used for the tags.

In operation, a sample collector is placed such that the sample is directly above the sample application zone 44. The sample (including the enzyme target, if present) is transferred onto the sample application zone 44. Then, buffer is preferably added to permit flow of the sample and the peptide (if released) to the detection zone 52. An immobilized tag 50 in the test zone 45 then binds the tag 8. Since the peptide 5 includes a label 9, the complex that forms is detectable and indicates a positive result. Proper operation of the test also results in a detectable positive result in the control zone 46 due to the interaction between a control zone binding partner and its immobilized partner in the control zone 46. Such control reagents are known in the art. In one preferred embodiment, the control conjugate is Chicken IgY conjugated to blue latex beads or colloidal gold and the control line in the control zone is Rabbit anti Chicken IgY. The control conjugate is preferably embedded into the test strip in the sample application zone 44; however, it may be located anywhere upstream of the control zone, such that it is transported to the control zone while the assay is run.

Although it is not shown, there may also optionally be a lysis zone, which preferably overlaps the sample application zone 44. In other embodiments, there may be a blocking zone that includes capturing reagents for capturing interferents.

In another embodiment, shown in FIGS. 2A through 2D and FIGS. 3A through 3C, the peptide substrate 105 and the sample are placed into a tube 160 or other container and enzyme cleavage occurs before the sample and peptide are transferred onto the lateral flow test strip.

Figure 5A:
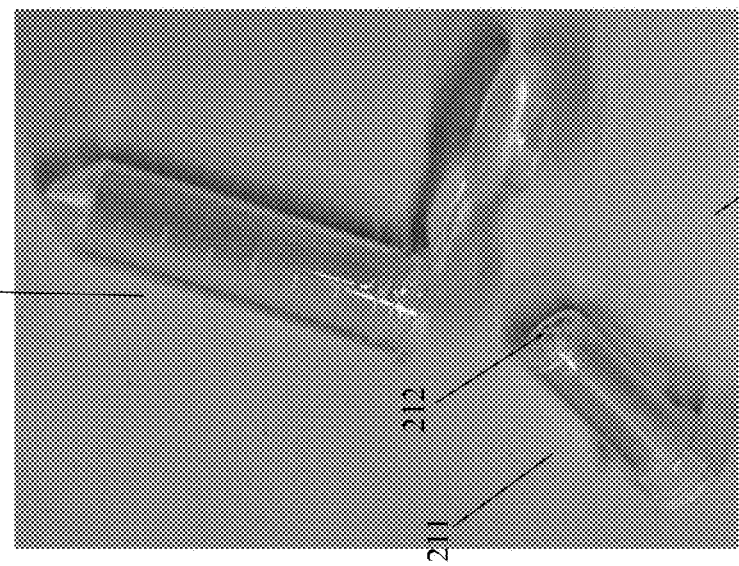
FIG. 5A shows centrifuge filter tubes (Alltech No. 24126, filter 0.2 μm).
Figure 5B:
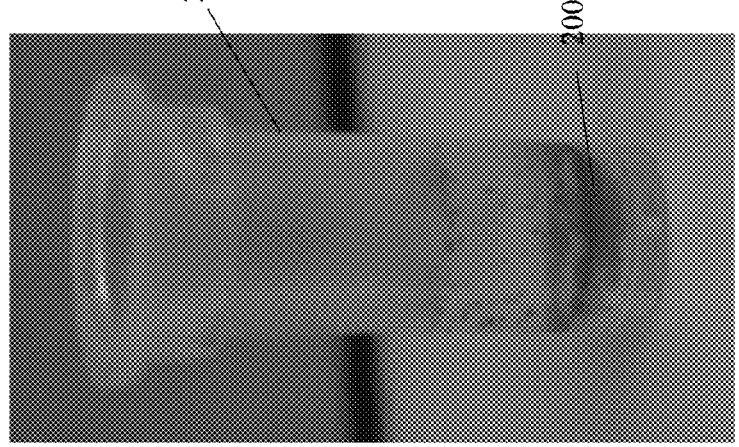
FIG. 5B shows a filter tube loaded with substrate NMFB1.
Figure 5C:
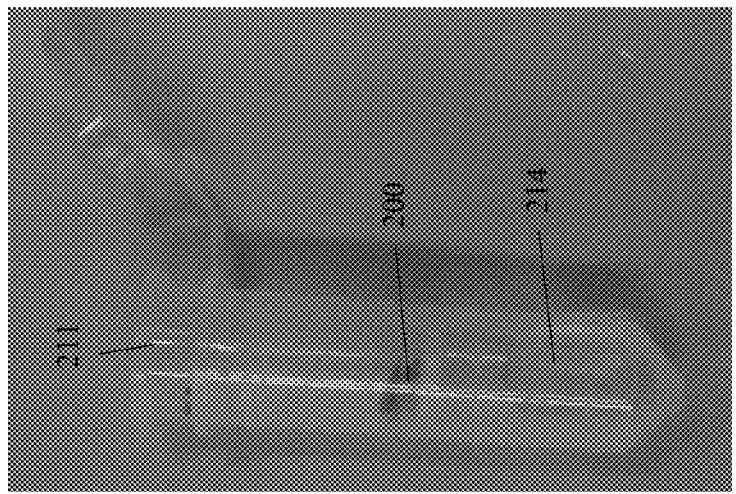
FIG. 5C shows that, due to the PEGA resin, the NMFB1 substrate remains in the filter tube after centrifugation.
Figure 6A:
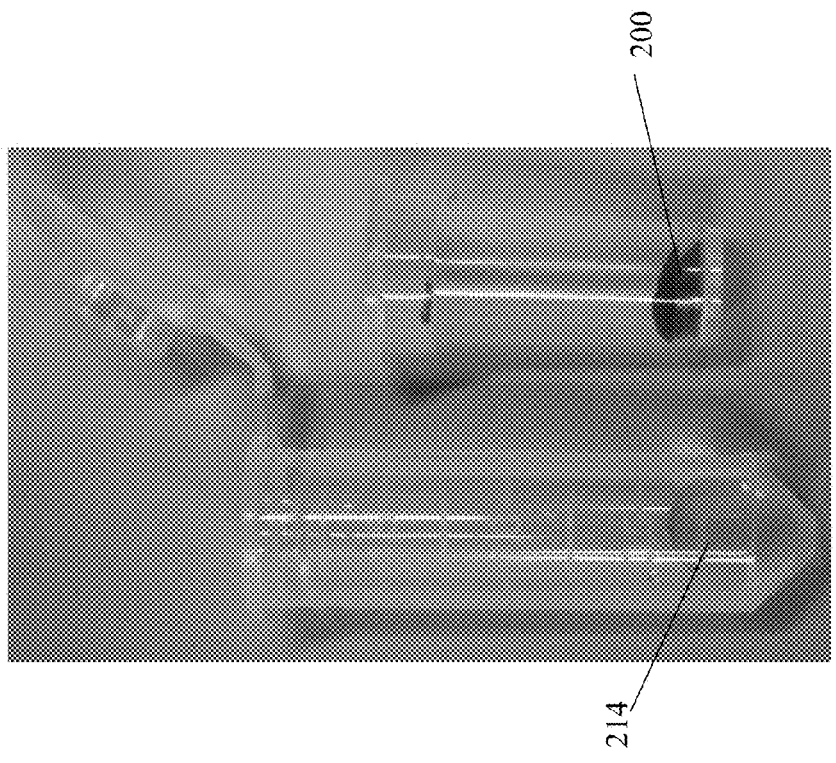
FIG. 6A shows NMFB1 at low pH after overnight incubation and filtration.
Figure 6B:
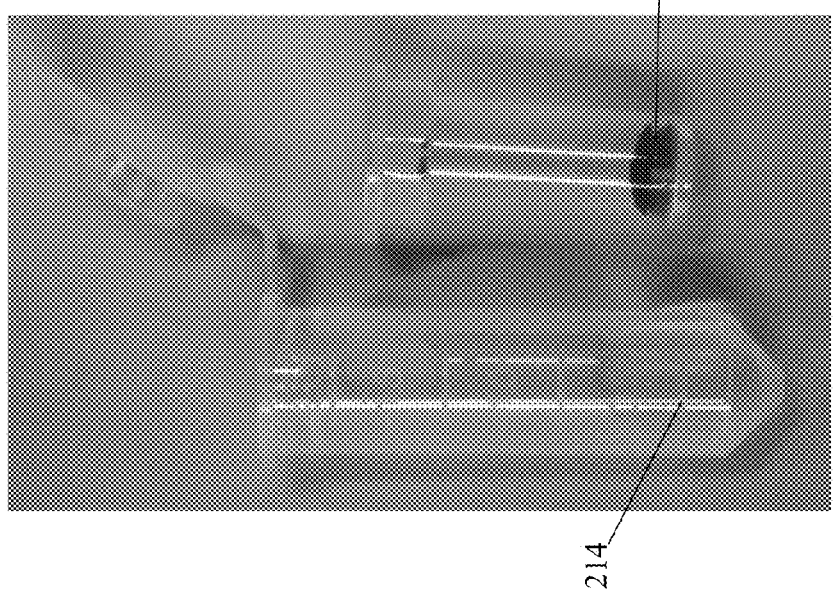
FIG. 6B shows the substrate in the presence of trypsin.
Figures 7A, 7B, 7C, 7D, 7E, 7F, 7G, 7H:
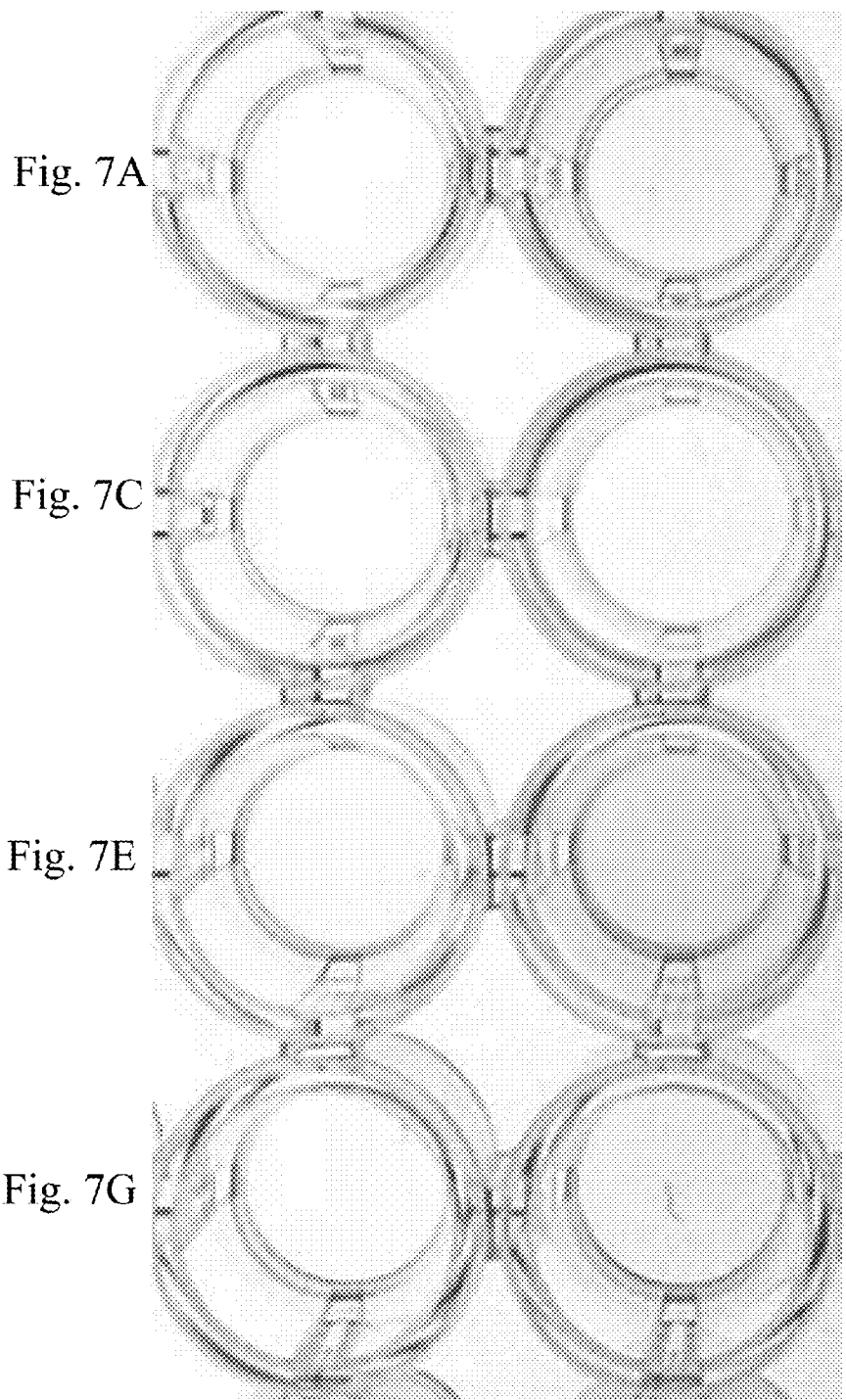
FIG. 7A shows the interior of an outer filter tube after incubation of the substrate with trypsin.
FIG. 7B shows the conditions of FIG. 7A, at low pH.
FIG. 7C shows the interior of an outer filter tube after incubation of the substrate without trypsin.
FIG. 7D shows the conditions of FIG. 7C, at low pH.
FIG. 7E shows the conditions of FIG. 7A, in the presence of 10% MeOH.
FIG. 7F shows the conditions of FIG. 7B, in the presence of 10% MeOH.
FIG. 7G shows the conditions of FIG. 7C, in the presence of 10% MeOH.
FIG. 7H shows the conditions of FIG. 7D, in the presence of 10% MeOH.

In this embodiment, a sample matrix is added to a reaction receptacle, shown as a tube 160 and extraction dropper 161 in FIGS. 3A and 3B, containing a trappable peptide complex (in solution or lyophilized). While a tube is shown in these figures, other alternative types of reaction systems, as known in the art, may be used to facilitate the reaction between the peptide and the target enzyme in the sample. Another example of a reaction receptacle is the tube 210 shown in FIGS. 5 and 6. There may also optionally be one or more lysis agents within the tube 160.

The tube 160 mates with the extraction dropper 161 to create a reaction chamber in which the sample and other reagents are placed so that a cleavage reaction can occur (if the target enzyme is present in the sample). The extraction dropper 161 preferably includes a tip 163 that transfers the sample to the sample application zone of the test strip. The tube 160 and extraction dropper 161 may be made of any material that can effectively hold samples and reagents. In some embodiments, the tube 160 and extraction dropper 161 are made of a squeezable material, such as plastic or another malleable material. The tip 163 may be made of any material that can serve as a "pre-filter" including, but not limited to, glass fibers, sintered glass, acetate, gauze, and cotton.

One of the reagents in the tube 160 is a trappable particle 101 bound to a peptide 105, which is preferably approximately 20 to 30 amino acids long. The peptide 105 includes at least one enzyme cleavage site 104. The enzyme cleavage site is specific to a target enzyme. For example, the enzyme may be specific to a bacteria that causes infection. One may choose a peptide 105 that is cleavable by an enzyme ubiquitous in many different bacterial strains, or an enzyme that is only found in one or two strains of bacteria. Peptides may be selectively engineered for one or two strains. The peptide may be made as specific as needed for the assay. The specificity of the assay depends on the enzyme chosen. For example, some enzymes are specific for multiple strains of bacteria, while other enzymes are specific to one or two particular strains of the bacteria. In other embodiments, the enzymes being tested for may be from viruses, or other sample components of interest.

The trappable peptide complex, shown in FIG. 2A, includes the trappable large particle 101, preferably at least 10 μm in size. The size of the trappable large particle 101 is chosen such that it can not pass through the filter 162 in the extraction dropper 161 of the tube 160.

The size of this particle 101 depends upon the porosity of the filter membrane 162. Any particle that is greater or equal to the porosity of the filter 162 membrane may act as the trappable particle 101. This means that, in the absence of the enzyme of interest, the cleavable peptide 105 remains bound to the trappable particle 101, and is not transferred to the sample application zone 44 of the test strip.

The peptide 105 is also bound to a tag 108 and a detectable label 109. In preferred embodiments, the detectable label 109 is a visible label, but other labels, as known in the art, may be used. In one preferred embodiment, a gold label is used. The tag 108 and the label 109 are both bound to the peptide 105 at a location on the side of the enzyme cleavage site opposite the side where the trappable particle 101 is located. In another embodiment, instead of being bound to a detectable label 109, the peptide 105 is dyed with a detectable label.

The test zone 45 in this embodiment includes an immobilized tag 50 that binds to the tag 108 bound to the cleaved peptide 105.

In one preferred embodiment, the peptide 105 is tagged with biotin 108. In embodiments where the tag 108 on the peptide 105 is biotin, the immobilized tag 50 in the detection zone is preferably avidin, neutravidin, or streptavidin. In other embodiments, the peptide 105 is tagged 108 with avidin, neutravidin, or streptavidin. In these embodiments, the immobilized tag 50 in the detection zone 52 is preferably biotin. Alternatively, the tag 108 on the peptide may be a lectin and the immobilized tag 50 may be a glycosyl moiety. For example, in some embodiments, the lectin is the Garden pea Lectin and the glycosyl moiety is an erythrocyte glycosyl unit. The tag on the peptide and the immobilized tag may be reversed within the spirit of the present invention. For example, the glycosyl moiety may be the tag on the peptide, with an immobilized lectin tag in the detection zone. In other embodiments, other receptors and ligands may be used for the tags.

In operation, if the trappable peptide complex is lyophilized, a buffer is then added. A filter 162 and extraction dropper 161 are assembled to the tube 160. A sufficient period of time is allowed for the enzymatic cleaving reaction to occur between the target enzyme and the substrate. If necessary, some agitation of the mixture occurs by moving the mixture in the tube 160. After sufficient time, the assembled device (shown in FIG. 3A) is inverted over the analysis cassette/test strip.

The filter 162 pore size is selected to allow the cleaved peptide 105 with the detectable label 109 and tag 108 (biotin, for example) to pass though the filter 162 and drop onto the sample application zone 44 of the test strip. The portion of the cleaved peptide 105 with the larger trapped particle 101 attached is unable to pass through the filter 162 and is retained in the filter/tube assembly. Similarly, if the target enzyme is not present, the peptide 105 remains bound to the trapped particle 101 and is unable to pass through the filter 162 onto the sample application zone 44 of the test strip.

When the target enzyme is present in the sample, the enzyme cleaves the peptide 105 at the enzyme cleavage site 104. The cleavage results in the portion of the peptide 105 no longer attached to the trappable particle 101 being transferred to the test trip, where it travels downstream to the detection zone 52. This peptide portion is shown in FIGS. 2C and 2D. There is an immobilized tag 50 in the test zone 45, which binds to the tag 108 on the peptide 105.

After a sufficient incubation period, the tube 160 is placed such that the extraction dropper tip 163 is directly above the sample application zone 44. The sample (including the peptide 105, if cleaved) is transferred onto the sample application zone 44. Then, buffer is preferably added to permit flow of the sample and the peptide (if cleaved) to the detection zone 52. An immobilized tag 50 in the test zone 45 then binds the tag 108. Since the peptide 105 includes a label 109, the complex that forms is detectable and indicates a positive result. Proper operation of the test also results in a detectable positive result in the control zone 46 due to the interaction between a control zone binding partner and its immobilized partner in the control zone 46. Such control reagents are known in the art. In one preferred embodiment, the control conjugate is Chicken IgY conjugated to blue latex beads or colloidal gold and the control line in the control zone is Rabbit anti Chicken IgY. The control conjugate is preferably embedded into the test strip in the sample application zone 44; however, it may be located anywhere upstream of the control zone, such that it is transported to the control zone while the assay is run.

In some embodiments, there may be a blocking zone on the test strip that includes capturing reagents for capturing interferents.

As shown in FIGS. 2B and 2D, these embodiments may use a universal test strip, that is not specific to any enzyme or target, because none of the reagents specific to the sample or target are found on the strip.

While the sample application zone 44 is separate from the test zone 45 in FIGS. 2B and 2D, the sample application zone 44 could alternatively overlap or completely coincide with the test zone 45 in these embodiments.

In an alternative embodiment, instead of the anchor system used in FIG. 1A through 1D or the filter system used in FIGS. 2A through 3C, the anchored peptide 5 or 105 is bound to a swab member through the anchor particle 1 or 101. The swab member is preferably placed into a device (e.g.—a tube or other reaction container) with the sample of interest. Similar to the earlier described embodiments, the peptide 5 or 105 remains bound to the swab member in the absence of the target enzyme. After a sufficient period of time has passed for the target enzyme to cleave the peptide and release it from the swab member, the swab member or the reaction liquid is placed on the sample application zone of a test strip or other sample analysis device, and preferably compressed to release the labeled, cleaved, tagged peptide (in the presence of the target enzyme). Once the labeled, cleaved, tagged peptide is on the strip, a positive result is shown by a detectable signal in the test zone, similar to the embodiments described above.

In another alternative embodiment, the anchored peptide complex could be placed on a sample compressor. Lateral flow assays with sample compressors are disclosed in U.S. Patent Publication No. 2011/0136258, entitled "Multiplanar Lateral Flow Assay with Sample Compressor", published Jun. 9, 2011 and herein incorporated by reference. In embodiments using the lateral flow assay systems disclosed in 2011/0136258, the peptide 5 or 105 may, through the anchor particle 1 or 101, be anchored on a pad separate from the test strip, the sample compressor, and the sample collector, anchored on the sample compressor pad, anchored on the sample collector, or anchored somewhere on the test strip where it will encounter the sample. The control conjugate in these embodiments is preferably on the sample compressor, but may alternatively be located elsewhere.

In all of the embodiments described herein, the anchored peptide complex/trappable peptide complex is in residence with the sample for a sufficient time for an enzymatic reaction to occur. The residence time (the amount of time the sample is in contact with the anchored/trappable peptide complex) is important, in order for sufficient enzymatic cleavage to occur to result in a clear positive signal at the test zone. In some preferred embodiments, the residence time is at least 10 minutes. In other preferred embodiments, the residence time is at least 15 minutes. In still other preferred embodiments, the residence time is at least 20 minutes.

In the embodiments of FIGS. 1A through 1D, the residence time is the time between when the sample has been added to the sample application zone and when buffer reaches the sample application zone. In the embodiments of FIGS. 2A through 3C, the residence time is the amount of time that the trappable peptide complex is in the tube with the sample. Similarly, in embodiments where the anchored peptide complex is on a swab member placed into a receptacle containing the sample, the residence time is the amount of time the swab member remains in the receptacle. In embodiments where the anchored peptide complex is on a sample compressor, the residence time is the time between when the sample is compressed by the vertical stack and when buffer reaches the stack.

As some examples for peptides 5 and 105 and enzyme targets for the assay, there are a number of known enzymes in the bacteria known to cause anthrax. *Bacillus anthracis*, a gram-positive, spore forming bacterium, is the causative agent of anthrax. The stability and infectious capacity of the spores gives *B. anthracis* the high potential to be used as a biological weapon. Inhaled *B. anthracis* spores germinate in the lungs leading to the emergence of vegetative *B. anthracis* into circulation. This systemic infection may result in secondary shock, multiple organ failure, and death. Early diagnosis is critical for effective treatment of inhalation anthrax. Current diagnostic tests take several hours from sample to test result. The methods and devices of the present invention can be used as a single-step non-invasive point-of-care (POC) diagnostic test. A rapid, simple-to-use POC test eliminates the need for the laboratory or powered equipment and enables broad field deployment of a rapid POC diagnosis test for anthrax inhalation infection as well as the rapid and specific analysis of environmental samples for the presence of *B. anthracis* spores.

Current methods for diagnosis of *B. anthracis* infection are laborious and not easily applicable in the field. Research has shown that the Lethal Factor (LF) from the toxin produced during *B. anthracis* infection possesses distinct protease activity, able to specifically cleave peptides derived from the bacteria's natural target substrate into well-defined products which may subsequently be analyzed sensitively by means of mass spectrometry. Analogous to this LF cleavage process, a particular peptide sequence (with acronym BIKKAM1, see EP2189536, entitled "Rapid FRET Based Anthrax Analysis", published May 26, 2010, incorporated herein by reference) is cleaved by a different enzyme complex present in the cell wall/membrane of *B. anthracis*. The BIKKAM1 peptide is highly selective for *B. anthracis*. Any of the substrates and peptides disclosed in EP2189536 which are specifically cleaved by enzymes from micro-organisms could be used herein to detect the presence of those micro-organisms.

TABLE 1

Peptides and their Bacterial Enzyme Targets

| EP2189536 Code | Formula | In vitro Cleavage Activity (using FRET) | Ex vivo Cleavage activity (using FRET) |
| --- | --- | --- | --- |
| BikKam 1 | FITC-Ahx-Leu-DLeu-Lys-DABCYL | *B. anthracis* | *B. anthracis, B. thuringiensis* (weak) |
| BikKam 2 | FITC-Ahx-DLeu-Leu-Lys-DABCYL | *B. anthracis, B. cereus* (weak), *B. thuringiensis* (weak) | *B. anthracis, B. thuringiensis* |
| BikKam 3 | FITC-Ahx-Leu-Leu-Lys-DABCYL | *B. globigii, C. botulinum, P. auruginosa, V. cholerae, E. herbicola* (indicates broad-spectrum detection of micro-organisms) | *B. anthracis, B. thuringiensis, V. cholerae, P. aeruginosa* (weak) |
| BikKam 4 | FITC-Ahx-DLeu-DLeu-Lys-DABCYL | *B. anthracis, B. thuringiensis* | *B. anthracis, B. thuringiensis* |
| BikKam 5 | FITC-Ahx-Leu-DLeu-Leu-Lys-DABCYL | *B. anthracis, V. cholerae* | *B. anthracis, B. thuringiensis* (weak) |
| BikKam 6 | FITC-Ahx-Leu-DVal-Lys-DABCYL | *B. anthracis* (moderate) | *B. anthracis* (moderate) |

TABLE 1-continued

Peptides and their Bacterial Enzyme Targets

| EP2189536 Code | Formula | In vitro Cleavage Activity (using FRET) | Ex vivo Cleavage activity (using FRET) |
|---|---|---|---|
| BikKam 7 | FITC-Ahx-Gly-DLeu-Lys-DABCYL | B. anthracis, B. thuringiensis (weak) | B. anthracis, B. thuringiensis |
| BikKam 8 | FITC-Ahx-Gly-DLeu-Lys-DABCYL | No significant enzyme activity with tested micro-organisms | No significant enzyme activity with tested micro-organisms |
| BikKam 9 | FITC-Ahx-Pro-Hyp-Lys-DABCYL | No significant enzyme activity with tested micro-organisms | No significant enzyme activity with tested micro-organisms |
| | FITC-Ahx-Gly-Gly-Gly-Gly-Lys-DABCYL | P. aeruginosa | P. aeruginosa |

In Table 1, FITC is a fluorescent label (fluorescein 5-isothiocyanate) and DABCYL is a quencher for the fluorescent label (4-((-4-(dimethylamino)-phenyl)-azo)-benzoic acid). Ahx is aminohexonic Acid, Leu is L-Leucine, DLeu is D-Leucine, Lys is L-Lysine, DVal is D-valine, Gly is L-glycine, DAla is D-alanine, Pro is L-proline, and Hyp is hydroxyproline. Since FRET is not used in the present invention, neither FITC nor DABCYL would be needed as part of the peptides being used in the assays of the present invention. Instead, the FITC would preferably be replaced by a visual label. However, FITC could be used if fluorescence is the manner in which the test results are being detected. Any of the peptides listed in Table 1 (or variations of these peptides without the FITC and/or the DABCYL components) may be used as the peptide 5 or 105 in embodiments of the present invention. Alternative peptides specific to enzymes of interest could also be engineered to detect particular organisms.

An Example Identifying Trypsin

As an example, a substrate is synthesized with the cleavage site for trypsin. FIG. 4 shows a substrate NMFB1 200. The substrate includes biotin 201, a protease substrate cleavage site 202, two PEG spacers 203, a visual marker DABCY (which creates a red color) 204, and a PEGA resin 205. The substrate NMFB1 200 is immobilized by the PEGA resin 205.

Two to three milligrams of the NMFB1 substrate 200 were incubated in PBS pH 7.4 in a total volume of 600 μl with 10 μl of trypsin (1 mg/ml) overnight at 37° C., gently rotating. The mixture was filtered by centrifugation filtration as shown in FIGS. 5 and 6. FIG. 5A shows centrifuge filter tubes 210 (Alltech No. 24126, filter pore size 0.2 μm) with an inner tube 211 containing the 0.2 um pores 212 and an outer tube 213 for receiving the filtered liquid 214 and any released substrate 200. The filter tubes 210 are examples of reaction receptacles. FIG. 5B shows a filter tube 211 loaded with the substrate 200. FIG. 5C shows that, due to the PEGA resin 205, the substrate 200 is immobilized on the resin 205 and remains in the inner filter tube 211 after centrifugation. As a result, the filtered liquid 214 contains no color.

0.2 N HCL was added to lower the pH below 4, increasing the visibility of the signal. FIG. 6A shows a view of the inner tube 212 separate from the outer tube 213 in the control with the NMFB1 substrate 200 at low pH after overnight incubation and filtration. All of the substrate 200 is still located in the inner tube 211 and the filtered liquid 214 contains no color. As discussed above, this indicates that the substrate 200 is immobilized on the resin 2005, trapping it in the inner filter tube 211. FIG. 6B shows the NMFB1 substrate 200 at low pH after overnight incubation and filtration in the presence of trypsin. In contrast to FIG. 6A, in this figure, the substrate 200 has been cleaved by the trypsin at the cleavage site 202, releasing the substrate 200 and permitting it to travel through the pores 212. The filtered liquid 214 is tinted red due to the visual marker DABCY 204 that is attached to the released substrate 200.

FIGS. 7A through 7H s show a visually assessed colorimetric assay under various experimental conditions with the substrate 200 with and without trypsin. The pH was lowered (FIGS. 7B and 7D) to enhance the signal. 10% methanol was added (FIGS. 7E through 7H) to enhance the signal even further. There was a slight background with the additional of methanol, which further increased at lower pH.

FIG. 7A shows NMFB1 200 after overnight incubation with trypsin in PBS. FIG. 7B shows the substrate 200 from FIG. 7A, at low pH. FIG. 7C shows a control, NMFB1 after overnight incubation in PBS, without trypsin. FIG. 7D shows the substrate 200 from FIG. 7C, at low pH. FIG. 7E shows the substrate 200 from FIG. 7A in the presence of 10% MeOH. FIG. 7F shows the substrate 200 from FIG. 7B in the presence of 10% MeOH. FIG. 7G shows the substrate 200 from FIG. 7C in the presence of 10% MeOH. FIG. 7H shows the substrate 200 from FIG. 7D in the presence of 10% MeOH.

The yellow tint seen in FIGS. 7A, 7C, and 7G was around the wall rather than at the bottom of the tube, and was not indicative of the presence of trypsin. Methanol by itself gives a very slight yellow color to the dye (FIG. 7E). Methanol and the lower pH further enhances this yellow color. Centrifugation does not remove the dye 100%. When the substrate is cleaved by trypsin and a lot more dye is in the supernatant, the color (pink or red) is in the well rather than on the sides only. FIG. 7B clearly shows a red tint in the well, at low pH in the presence of trypsin. The pink or red is even more pronounced in FIG. 7F, at low pH with the addition of 10% MeOH. In contrast, the controls shown in FIGS. 7C, 7D, and 7G, show little or no color. While FIG. 7H does show some pink/red color, the intensity of the color in this figure (without trypsin, at a low pH and with 10% MeOH) is less than the intensity shown in FIG. 7B (with trypsin, at a low pH, but no 10% MeOH) and significantly less than the intensity shown in FIG. 7F, which included identical conditions to the conditions in FIG. 7H. While the addition of 10% Methanol increases the background, the difference between the control (FIG. 7H) and with trypsin (FIG. 7F) is significant.

The filtered liquid 214 in each of these examples can be transferred to a sample analysis device. Since the substrate 200 includes biotin 201 (a first tag), when avidin (an immobilized second tag) is present in the test zone of the sample analysis device, it binds to the biotin 201 on the released substrate 200, thus producing a detectable signal for the samples including trypsin.

The testing described in this example shows the use of the method and a reaction receptacle with a "model" enzyme such as trypsin. Differing amounts of methanol or different solvents could be used to enhance the signal while decreasing the background.

The elimination of enzyme isolation improves the speed of analysis of the current methods and enables the assay system to be integrated into an easy-to-use POC format. The same assay may be used for detection of gastrointentistinal, cutaneous, or inhalational (resulting from aerolization of *B. anthracis* spores) anthrax infection.

Using the methods and devices of the present invention, a discrete single-step rapid assay produces a test result within minutes with no operator intervention. This assay is simple to use by untrained personnel. An additional unique feature is the possible use of the proposed device with non-invasive bronchial lavage samples. Bronchial lavage samples have been shown to provide earlier indication of an anthrax infection. In addition, a similar set-up is applicable to detection of bacterial toxins with protease activity, such as Botulinum toxin.

The FRET analysis in EP2189536 was done by testing the enzyme activity of bacterial supernatants by incubating the FRET peptides with supernatants in 96-well plates. In contrast, the methods and devices of the present invention use lateral flow assays to test for the presence of the microorganisms. In addition, unlike the FRET analysis taught in EP 2189536, the methods and devices of the present invention may be read visually, which eliminates the need for a fluorescent reader. In addition, there are no additional reagents, such as quenchers, needed.

Accordingly, it is to be understood that the embodiments of the invention herein described are merely illustrative of the application of the principles of the invention. Reference herein to details of the illustrated embodiments is not intended to limit the scope of the claims, which themselves recite those features regarded as essential to the invention.

What is claimed is:

1. A lateral flow assay system for detecting a target enzyme in a sample, comprising:

a) a reaction receptacle comprising:
  i) a tube and an extraction dropper;
  ii) at least one chamber for reaction between the sample and a trapped peptide complex, wherein the trapped peptide complex comprises:
    A) a trappable particle;
    B) a peptide bound to the trappable particle, wherein the peptide includes at least one enzyme cleavage site for a target enzyme;
    C) at least one detectable label coupled to the peptide; and
    D) at least one first tag bound to the peptide on a side of the enzyme cleavage site opposite the trappable particle; and
  iii) at least one filter located in the extraction dropper, with a pore size that is smaller than a size of the trappable particle;
  wherein the tube mates with the extraction dropper to create the chamber; and
b) a sample analysis device comprising:
  i) a sample application zone for receiving the reacted sample and peptide from the reaction receptacle; and
  ii) a test zone comprising at least one immobilized second tag that binds to the first tag;
  wherein, when the target enzyme is present in the sample, the enzyme cleaves the peptide at the enzyme cleavage site such that the peptide can pass through the filter and be transferred from the reaction receptacle to the sample application zone of the sample analysis device, and the first tag binds to the immobilized second tag in the test zone such that the label is detectable in the test zone; and
  wherein, when the target enzyme is not present in the sample, the peptide is trapped in the reaction receptacle by the filter and is not transferred to the sample analysis device, such that there is no detectable signal in the test zone when an assay has been run.

2. The lateral flow assay system of claim 1, wherein the sample analysis device is a chromatographic test strip.

3. The lateral flow assay system of claim 1, wherein the detectable label is a visible label.

4. The lateral flow assay system of claim 1, wherein the peptide is dyed with the detectable label.

5. The lateral flow assay system of claim 1, wherein the detectable label is bound to the peptide on a side of the enzyme cleavage site opposite the trappable particle.

6. The lateral flow assay system of claim 1, wherein the first tag and the second tag comprise a pair selected from the group consisting of:

a) a first biotin tag and a second immobilized tag selected from the group consisting of avidin, neutravidin, and streptavidin;
b) a first tag selected from the group consisting of avidin, neutravidin, and streptavidin and a second biotin immobilized tag;
c) a first lectin tag and a second glycosyl moiety immobilized tag; and
d) a first glyosyl moiety tag and a second lectin immobilized tag.

7. The lateral flow assay system of claim 1, wherein the extraction dropper comprises a tip that transfers the reacted sample from the reaction receptacle to the sample analysis device.

8. The lateral flow assay system of claim 1, wherein the target enzyme is an enzyme from *B. anthracis*.

9. The lateral flow assay system of claim 1, wherein the enzyme cleavage site comprises a BIKKAM peptide selective for *B. anthracis*.

10. A lateral flow assay system for detecting an enzyme from *B. anthracis* in a sample, comprising:

a) a reaction receptacle comprising:
  i) at least one tube including at least one chamber for reaction between the sample and a trapped peptide complex, wherein the trapped peptide complex comprises:
    A) a trappable particle;
    B) a peptide bound to the trappable particle, wherein the peptide includes at least one enzyme cleavage site for the enzyme from *B. anthracis;*
    C) at least one detectable label coupled to the peptide; and
    D) at least one first tag bound to the peptide on a side of the enzyme cleavage site opposite the trappable particle; and
  ii) at least one filter with a pore size that is smaller than a size of the trappable particle; and
b) a sample analysis device comprising:
  i) a sample application zone for receiving the reacted sample and peptide from the reaction receptacle; and
  ii) a test zone comprising at least one immobilized second tag that binds to the first tag;

wherein, when the enzyme from *B. anthracis* is present in the sample, the enzyme cleaves the peptide at the enzyme cleavage site such that the peptide can pass through the filter and be transferred from the reaction receptacle to the sample application zone of the sample analysis device, and the first tag binds to the immobilized second tag in the test zone such that the label is detectable in the test zone; and wherein, when the enzyme from *B. anthracis* is not present in the sample, the peptide is trapped in the reaction receptacle by the filter and is not transferred to the sample analysis device, such that there is no detectable signal in the test zone when an assay has been run.

11. The lateral flow assay system of claim 10, wherein the sample analysis device is a chromatographic test strip.

12. The lateral flow assay system of claim 1, wherein the detectable label is a visible label.

13. The lateral flow assay system of claim 10, wherein the peptide is dyed with the detectable label.

14. The lateral flow assay system of claim 10, wherein the detectable label is bound to the peptide on a side of the enzyme cleavage site opposite the trappable particle.

15. The lateral flow assay system of claim 10, wherein the first tag and the second tag comprise a pair selected from the group consisting of:
   a) a first biotin tag and a second immobilized tag selected from the group consisting of avidin, neutravidin, and streptavidin;
   b) a first tag selected from the group consisting of avidin, neutravidin, and streptavidin and a second biotin immobilized tag;
   c) a first lectin tag and a second glycosyl moiety immobilized tag; and
   d) a first glyosyl moiety tag and a second lectin immobilized tag.

* * * * *